(12) United States Patent  
Magen et al.

(10) Patent No.: US 11,872,409 B2  
(45) Date of Patent: Jan. 16, 2024

(54) RADIOTHERAPY TEMPLATE ASSEMBLY

(71) Applicant: ALPHA TAU MEDICAL LTD., Jerusalem (IL)

(72) Inventors: Ofer Magen, Matan (IL); Niv Dana, Givatayim (IL); Sagy Tal, Tel Mond (IL); Amnon Gat, Matan (IL); Robert Den, Merion Station, PA (US)

(73) Assignee: ALPHA TAU MEDICAL LTD., Jerusalem (IL)

( * ) Notice: Subject to any disclaimer, the term of this patent is extended or adjusted under 35 U.S.C. 154(b) by 0 days.

(21) Appl. No.: 17/925,838

(22) PCT Filed: Oct. 27, 2021

(86) PCT No.: PCT/IB2021/059920  
§ 371 (c)(1),  
(2) Date: Nov. 17, 2022

(87) PCT Pub. No.: WO2022/101728  
PCT Pub. Date: May 19, 2022

(65) Prior Publication Data  
US 2023/0264042 A1 Aug. 24, 2023

Related U.S. Application Data

(60) Provisional application No. 63/112,676, filed on Nov. 12, 2020.

(51) Int. Cl.  
*A61N 5/10* (2006.01)

(52) U.S. Cl.  
CPC ......... *A61N 5/1007* (2013.01); *A61N 5/1014* (2013.01); *A61N 2005/1012* (2013.01); *A61N 2005/1018* (2013.01)

(58) Field of Classification Search  
CPC .... A61N 5/1001; A61N 5/107; A61N 5/1014; A61N 2005/1012; A61N 2005/1018  
See application file for complete search history.

(56) References Cited

U.S. PATENT DOCUMENTS

| 4,427,005 A * | 1/1984 | Tener ................... A61N 5/1007 604/116 |
| 7,425,194 B2 | 9/2008 | Baltas et al. |

(Continued)

FOREIGN PATENT DOCUMENTS

| WO | 2016009312 A1 | 1/2016 |
| WO | 2016087946 A1 | 6/2016 |

(Continued)

OTHER PUBLICATIONS

"Breast Bridge SET0080," Catalogue HDR Applicators + Accessories, PD13D113/Rev.12/09.2019, Eckert & Ziegler Bebig, pp. 1-2, year 2019, as downloaded from https://www.bebig.com/fileadmin/bebig_neu/user_uploads/Products/HDR_Brachytherapy/Breast_Bridge_EN_.pdf.

(Continued)

*Primary Examiner* — Samuel G Gilbert  
(74) *Attorney, Agent, or Firm* — Kligler & Associates Patent Attorneys Ltd.

(57) ABSTRACT

A template assembly including a first grid (22) for placement on a first side of a body organ, defining a plurality of apertures (329) adapted to receive elongate applicators (410), a second grid (24) for placement on a second side of a body organ, defining a plurality of apertures (34), adapted to receive applicators passing through apertures of the first grid and the body organ and at least one frame (26) defining a large hole (72), positioned between the first and second grids and configured to grasp the body organ.

18 Claims, 5 Drawing Sheets

(56) References Cited

U.S. PATENT DOCUMENTS

| | | |
|---|---|---|
| 8,834,837 B2 | 9/2014 | Kelson et al. |
| 9,694,202 B2 | 7/2017 | Helle et al. |
| 2003/0130573 A1 | 7/2003 | Yu et al. |
| 2009/0136422 A1 | 5/2009 | Kelson et al. |
| 2010/0249487 A1 | 9/2010 | Hermann et al. |
| 2012/0108882 A1 | 5/2012 | Hoedl |
| 2012/0277519 A1 | 11/2012 | Mehta et al. |
| 2014/0275964 A1 | 9/2014 | Kim |
| 2019/0022410 A1 | 1/2019 | Hermann et al. |
| 2021/0393979 A1* | 12/2021 | Valentini .............. A61N 5/1007 |

FOREIGN PATENT DOCUMENTS

| | | |
|---|---|---|
| WO | 2018165480 A1 | 9/2018 |
| WO | 2018229599 A1 | 12/2018 |
| WO | 2019171308 A1 | 9/2019 |

OTHER PUBLICATIONS

International Application # PCT/IB2021/059920 Search Report dated Feb. 16, 2022.
CN Application # 202180074842X Office Action dated Oct. 28, 2023.

* cited by examiner

RADIOTHERAPY TEMPLATE ASSEMBLY

CROSS-REFERENCE TO RELATED APPLICATIONS

The present application claims the benefit of U.S. Provisional Application 63/112,676, entitled "Brachytherapy template assembly", filed on Nov. 12, 2020, whose disclosure is incorporated herein by reference in its entirety.

FIELD OF THE INVENTION

The present invention relates generally to radiotherapy and particularly to methods and devices for implantation of radiotherapy sources.

BACKGROUND OF THE INVENTION

Radiation is used to kill cancerous or other malignant cells forming a tumor. Different methods are known for delivery of the radiation to the cancerous cells, including implanting radiation emitting seeds in the tumor. U.S. Pat. No. 8,834,837 and US patent publication 2009/0136422, which are incorporated herein by reference in their entirety, describe the use of a radioactive substance which emits alpha radiation, together with daughter nuclei of the radioactive substance, as a source for cell killing radiation. This method of radiation delivery is referred to herein as DaRT (Diffusing alpha-emitter radiation therapy).

In order to accurately position the seeds in a tumor in a body organ, it has been suggested to provide templates with multiple apertures for guiding applicators carrying the seeds into the tumor. The templates also generally serve as compression members which grasp the body organ so it does not move relative to the templates.

US patent publication 2019/0022410 to Hermann et al., titled: "Brachytherapy Apparatus and Methods for using them", describes a system including templates and compression members for directing needles into the tumor. The compression members include a hole pattern similar to that of the templates to allow passage of the needles. In order to anchor the seeds, the seeds are temporarily secured to a distal one of the compression members.

SUMMARY OF THE INVENTION

An aspect of some embodiments of the present invention relates to a template assembly, comprising a first grid for placement on a first side of a body organ, defining a plurality of apertures adapted to receive elongate applicators, a second grid for placement on a second side of a body organ, defining a plurality of apertures, adapted to receive applicators passing through apertures of the first grid and the body organ, and at least one frame defining a large hole, positioned between the first and second grids and configured to grasp the body organ. Optionally, the template assembly further incudes a bar on which the first grid, the second grid and the at least one frame are mounted. Optionally, the second grid is removably mounted on the bar. Optionally, the at least one frame is removably mounted on the bar. Optionally, the large hole covers at least 25% of an area of the at least one frame or even at least 50% of an area of the at least one frame. Optionally, the first and second grids and the at least one frame have a triangular shape. Optionally, the frame is configured to grasp the body organ, between the frame and one of the first and second grids. Optionally, the template assembly further incudes an additional frame defining a large hole, positioned between the first and second grids, wherein the body organ is grasped between the frame and the additional frame. Optionally, the at least one frame comprises an open frame. Optionally, the at least one frame is coupled to the first grid through a first bridge and to the second grid through a second bridge, separate from the first bridge.

An aspect of some embodiments of the present invention relates to a method of inserting brachytherapy seeds into a body organ, comprising grasping a body organ between a frame defining a large central hole, and an additional element, placing a grid defining a plurality of apertures adapted to receive elongate applicators, on one side of the body organ, passing a plurality of applicators through apertures in the first and second grids and through the body organ; and anchoring the brachytherapy seeds in the organ through the frame.

Optionally, the additional element comprises the grid. Optionally, placing the grid comprises placing the grid behind the frame. Optionally, placing the grid comprises placing a first grid behind the frame and placing a second grid defining a plurality of apertures adapted to receive the elongate applicators, on an opposite side of the organ from the first grid, and the method further comprising removing the first grid, in a manner allowing access to the body organ through the frame, after passing a plurality of applicators through the apertures, but before anchoring the brachytherapy seeds. Optionally, the additional element is the second grid. Optionally, the first and second grids and the at least one frame have a triangular shape. Optionally, the additional element comprises an additional frame.

DETAILED DESCRIPTION OF EMBODIMENTS

An aspect of some embodiments of the invention relates to a radiotherapy template assembly in which the task of grasping an organ is performed on at least one side by a frame which defines a large hole through which a medical practitioner can access the organ. Thus, the grasping of the organ continues even when one or more of the grid plates is removed, and is carried out without obstructing access of the medical practitioner to the organ.

Figure 1:
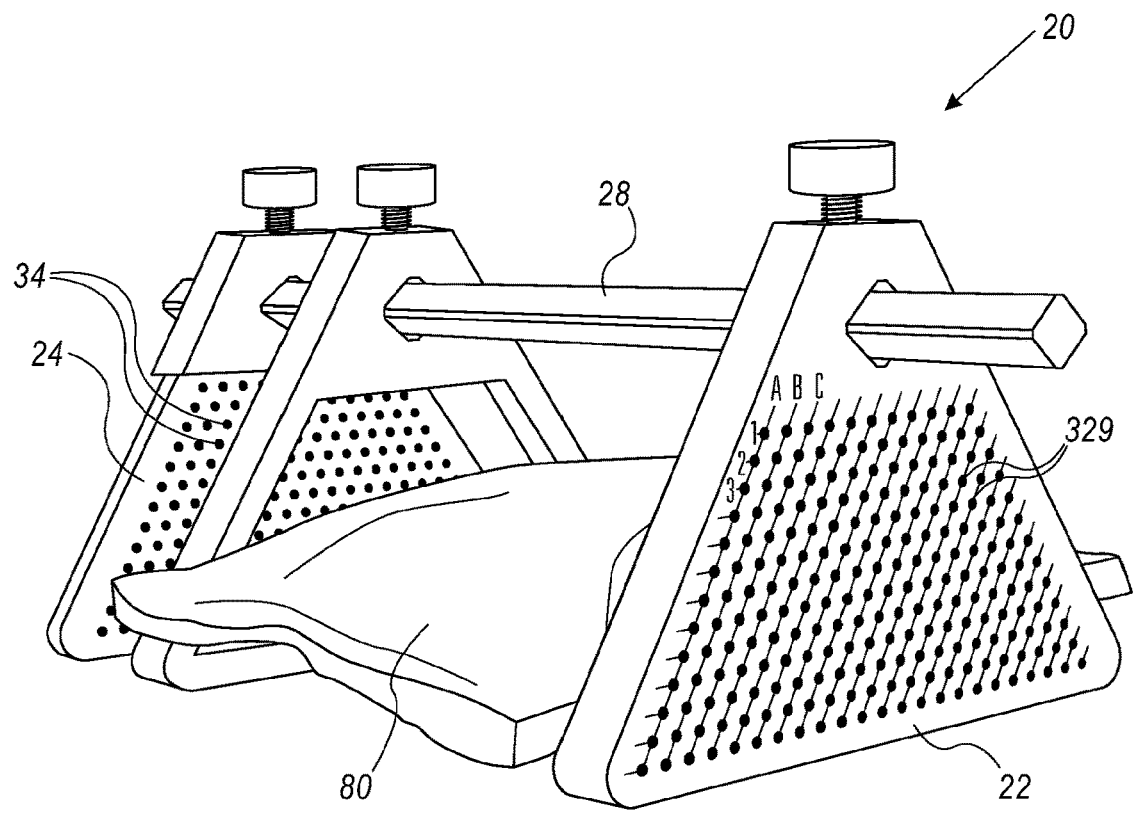
FIG. 1 is a schematic illustration of a radiotherapy template assembly, in accordance with an embodiment of the present invention.

FIG. 1 is a schematic illustration of a radiotherapy template assembly 20, in accordance with an embodiment of the present invention. Template assembly 20 comprises an insertion grid plate 22, which defines a plurality of apertures 329, through which applicators carrying radiotherapy seeds are inserted into an organ that is to receive radiotherapy treatment. Template assembly 20 further includes a leading grid plate 24, which defines a plurality of apertures 34, intended to receive the applicators inserted through apertures 329 of the insertion grid plate 22, on an opposite side of a treated organ 80. Template assembly 20 optionally further includes a bridge 28 on which grid plates 22 and 24 are slidably mounted. In some embodiments, grid plates 22 and 24 define respective holes 42 and 44 (FIG. 2) designed to receive bridge 28 and thus allow sliding of grid plates 22 and 24.

In accordance with embodiments of the present invention, template assembly 20 includes a frame plate 26, designed to grasp the body organ, in a manner similar to insertion grid plate 22, while allowing access to the organ, for example through a central hole 72. Optionally, frame plate 26 is configured to slide on bridge 28, for example by including a hole 46, through which bridge 28 slides, in a manner similar to grid plates 22 and 24. Frame plate 26 is mounted on bridge 28 between insertion grid plate 22 and leading grid plate 24, such that it can grasp an organ with insertion grid plate 22 from opposite sides of the organ.

Optionally, plates 22, 24 and 26 include respective screws 52, 54 and 56 for locking the plate relative to bridge 28, at a desired location along the length of the bridge. It is noted that screws are just one possible locking element that may be used and any other suitable locking element may be used, such as nails.

Figure 2:
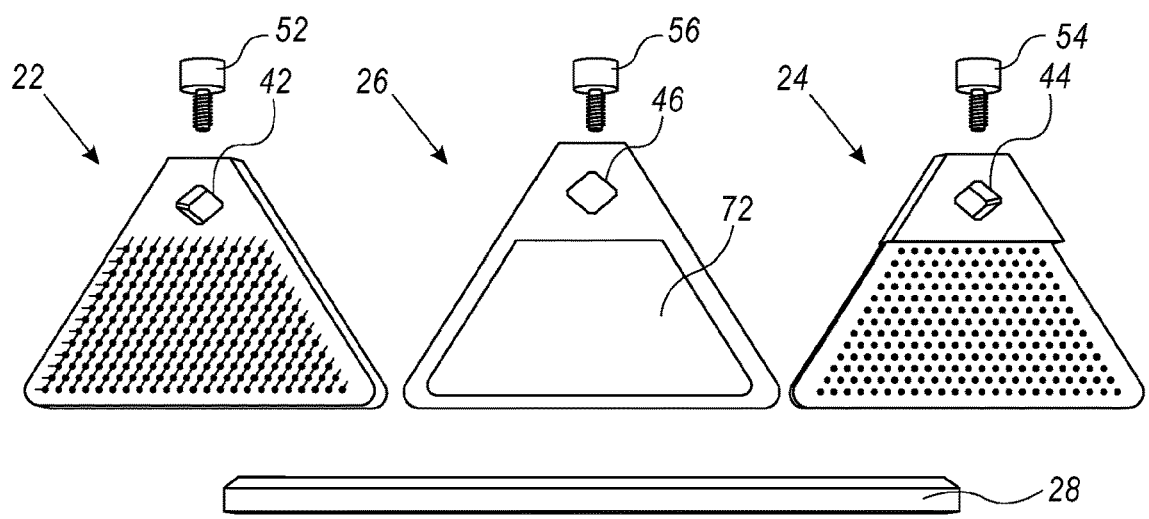
FIG. 2 is a schematic illustration of the elements of the template assembly of FIG. 1, in accordance with an embodiment of the present invention.

FIG. 2 is a schematic illustration of elements of template assembly 20, in accordance with an embodiment of the present invention. As shown, plates 22, 24 and 26 have a triangular shape, which is truncated at its narrow side where it defines holes 42, 44 or 46, through which bridge 28 passes. Alternatively, Plates 22, 24 and 26 have other shapes, such as square, rectangular, circular, oval, or polygon (e.g., hexagon) shapes, or an irregular shape. Holes 42, 44 and 46 may be defined within the shaped area of the plate, or may be defined in a narrow extension of the plates. The shape of plates 22, 24 and 26 is optionally selected to match the organ being treated in a manner which best grasps the organ between two of the plates 22, 24 and 26 and/or allows insertions of a required number and arrangement of applicators into the tumor.

In some embodiments, plates 22, 24 and 26 all have the same shape. In other embodiments, some or all of the plates have different shapes. For example, in one embodiment, plates 22 and 24 have the same shape, in order to simplify the matching of apertures and passing applicators through corresponding apertures, while frame plate 26 has a different shape which is designed for optimizing the task of grasping the body organ, while allowing access to the organ.

Frame plate 26 is optionally flat with the same layout over its entire thickness. Alternatively, frame plate 26 may have a three-dimensional structure with different layouts at different cross-sections of its thickness. The shape of frame plate 26 is optionally selected to best grasp the organ which it is intended to grasp, despite its large central hole 72.

Central hole 72 optionally has an area of at least 25%, at least 35%, at least 50% or even at least 60% of the area of frame plate 26. Central hole 72 optionally has an area of at least 3 $cm^2$, at least 5 $cm^2$, at least 8 $cm^2$, or even at least 12 $cm^2$.

Figure 3:
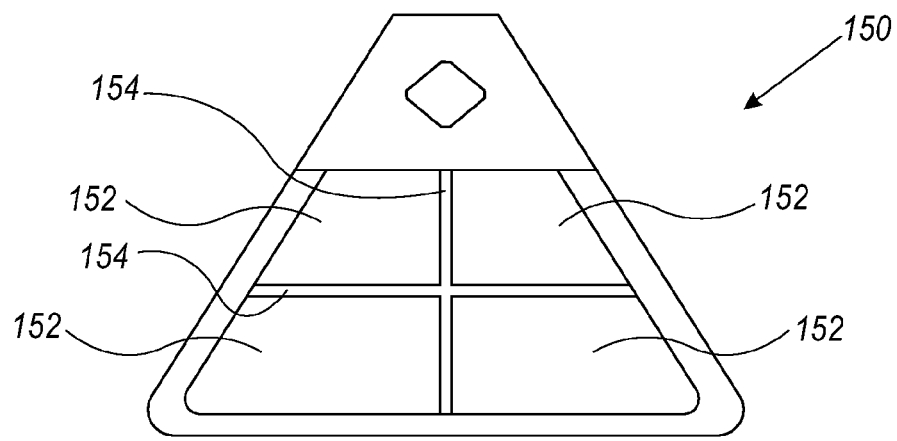
FIG. 3 is a schematic illustration of frame grid, in accordance with another embodiment of the present invention.

FIG. 3 is a schematic illustration of a frame plate 150, in accordance with another embodiment of the present invention. Frame plate 150 differs from frame plate 26 in that instead of a single central hole 72, frame plate 150 includes a plurality of medium size holes 152. Each of the medium size holes 152 optionally has an area of at least 2 $cm^2$, at least 3 $cm^2$, or even at least 5 $cm^2$. The medium size holes 152 may all have the same size and/or shape or different ones of the medium size holes 152 have different areas or shapes. Frame plate 150 optionally defines at least two, at least three or even at least four medium size holes. The separation 154 between the medium size holes 152 optionally takes part in the grasping of the organ. The separation between the medium size holes 152 is optionally relatively thin, in order to minimize the obstruction to access to the organ.

In some embodiments, central hole 72 or medium size holes 152 have an area which covers all the apertures 329 of grid plates 22 and 24, such that applicators inserted to any of the apertures 329 in grid 22 will pass through central hole 72 into the body organ. Alternatively, central hole 72 or medium size holes 152 have an area which covers fewer than all the apertures 329 of grid plate 22. Optionally, in this alternative, apertures 329 which do not correspond to the area of central hole 72 or medium size holes 152 are marked as not for use. In other embodiments, template assembly 20 is provided with a plurality of alternative frame plates 26 or 150 with central holes 72 or medium size holes 152 of different sizes and/or layouts. A physician selects one of the frame plates 26 or 150 which matches the apertures which are to be used in the treatment. In some embodiments, one or more of the frame grids 26 or 150 has a central hole 72 or medium size holes 152 which covers fewer than all the apertures 329 of grid plate 22, but covers at least 75%, at least 80% or even at least 90% of the apertures 329.

As mentioned above, insertion grid plate 22 defines a plurality of apertures 329. The apertures 329 are sized and shaped to allow insertion of applicators through them in an accurate manner. In some embodiments, apertures 329 are arranged in a hexagonal arrangement, in which each aperture 329 is located at vertices of equilateral triangles, having a length 166. Hexagons are formed by bisectors to the lines connecting the apertures 329 to their six nearest neighboring apertures. Optionally, the length 166 between adjacent apertures 329 is smaller than 5 millimeters, not greater than 4.5 millimeters, not greater than 4 millimeters, not greater than 3.5 millimeters, or even not greater than 3 millimeters. Alternatively, apertures 329 are arranged in any other suitable arrangement, such as a rectangular or circular array. Insertion grid plate 22 optionally defines at least 10, at least 20, at least 50 or even at least 100 apertures 329.

The arrangement of apertures 34 on leading grid plate 24 is optionally the same as the arrangement of apertures 329 on insertion grid plate 22. Alternatively, apertures 34 are arranged on leading grid plate 24 in a different arrangement than apertures 329 on insertion grid plate 22. Leading grid plate 24 optionally defines at least 10, at least 20, at least 50 or even at least 100 apertures 34. Apertures 329 and 34 have any suitable diameter needed for the specific applicator used and treatment specifications. In one example embodiment, apertures 329 and 34 have a diameter of about 1.35 mm Optionally all the apertures 329 and 34 have the same diameter. Alternatively, different apertures 329 have different sizes, different apertures 34 have different sizes and/or the apertures 329 have different sizes than apertures 34.

Optionally, insertion grid plate 22 includes row and/or column markings for addressing the apertures 329. Any suitable markings may be used including letters, numbers and/or colors. Generally, markings are not included on leading grid plate 24. In some embodiments, however, markings are included also on leading grid plate 24, to allow for simple insertion of the applicators through either of plates 22 and 24, and/or to allow for simple verification that an applicator passed on its way out through the correct aperture in leading grid plate 24.

The elements of assembly 20 comprise any suitable biocompatible material, such as plastic and/or metal. The details of insertion grid plate 22, leading grid plate 24 and/or bridge 28, such as materials and structure, are optionally in accordance with any suitable templates and/or bridges known in the art, such as described in US patent publication 2010/0249487 to Hermann et al., U.S. Pat. No. 7,425,194 to Baltas et al., and/or the white paper, Breast Bridge Set0080, P13D113/Rev.12/September 2019, Eckert & Zeigler Bebig, the disclosures of which are incorporated herein by reference.

In some embodiments, insertion grid plate 22 and leading grid plate 24 have the same structure. In other embodiments, grid plates 22 and 24 have different structures, for example one is thicker than the other. Optionally, insertion grid plate 22 is thicker than leading grid plate 24, in order to guide the applicators with greater support and control, and more accurately hold the inserted applicators.

Figure 4:
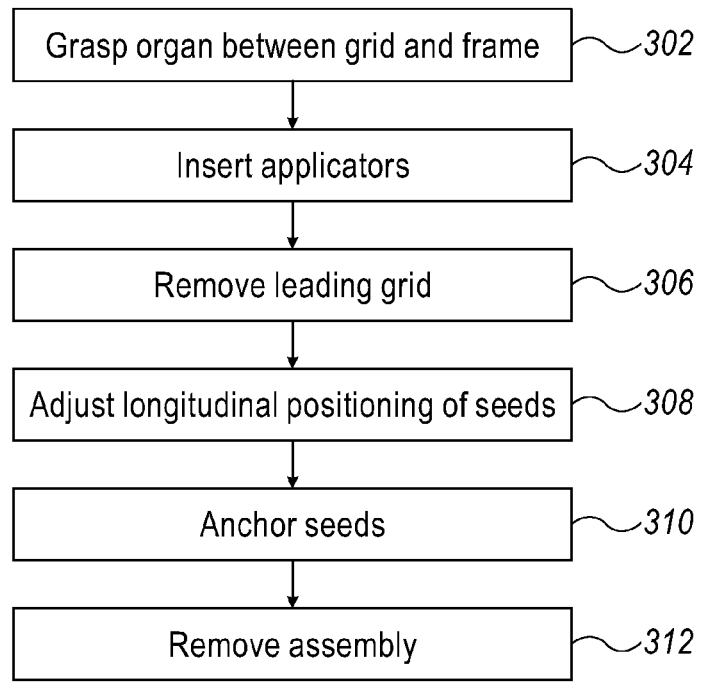
FIG. 4 is a flowchart of a method of implanting seeds for radiotherapy treatment in a body organ, in accordance with an embodiment of the present invention.

FIG. 4 is a flowchart of a method of implanting seeds for radiotherapy treatment in a body organ, using radiotherapy template assembly 20, in accordance with an embodiment of the present invention. Reference is also made to FIGS. 5A-5D which show organ 400 and template assembly 20 at different stages of the method.

Figure 5A:
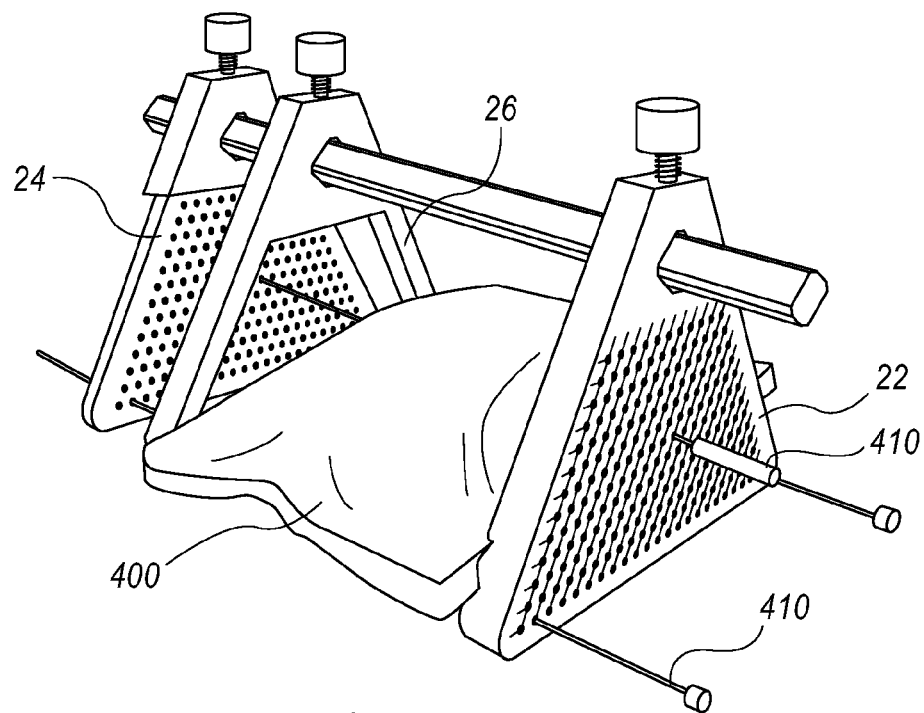
FIGS. 5A-5D show an organ being treated using the template assembly of FIG. 1 in accordance with the method of FIG. 4, at various steps of the treatment, in accordance with an embodiment of the present invention.
Figure 5B:
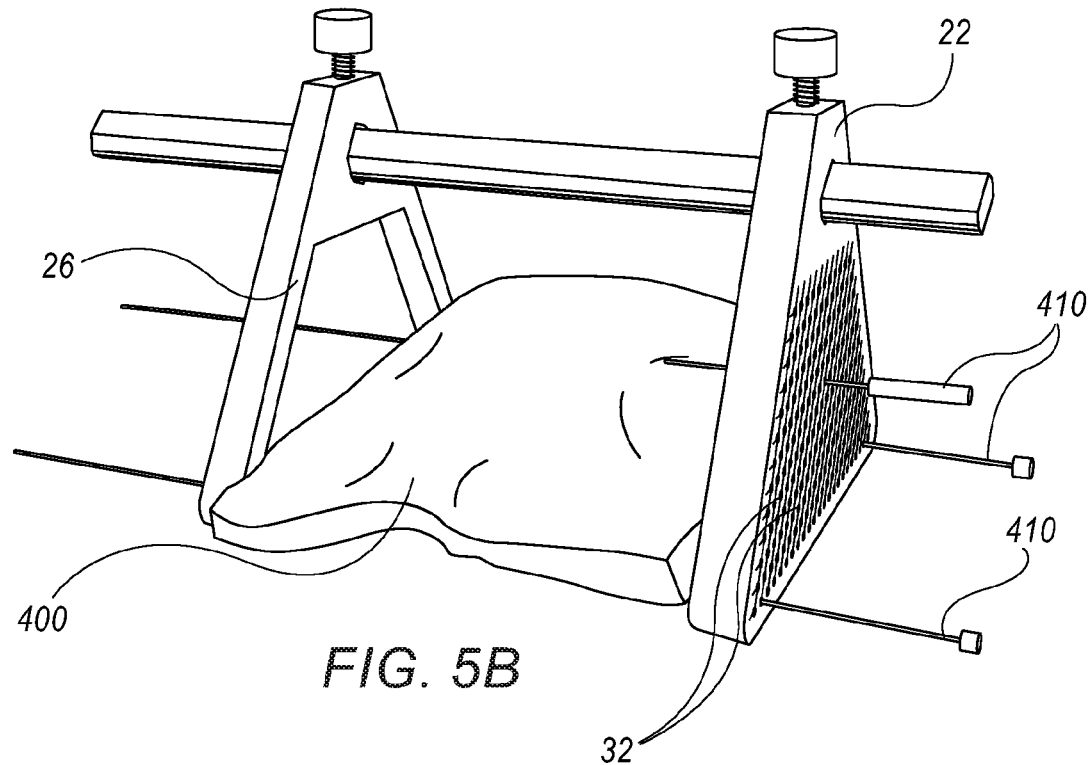
Figure 5C:
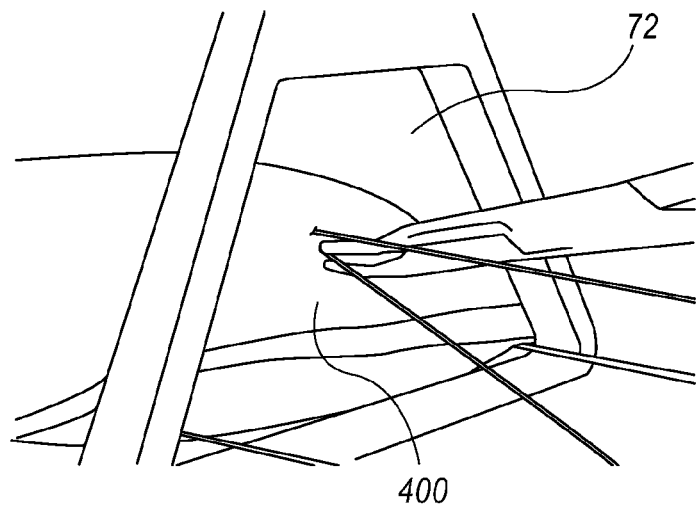
Figure 5D:
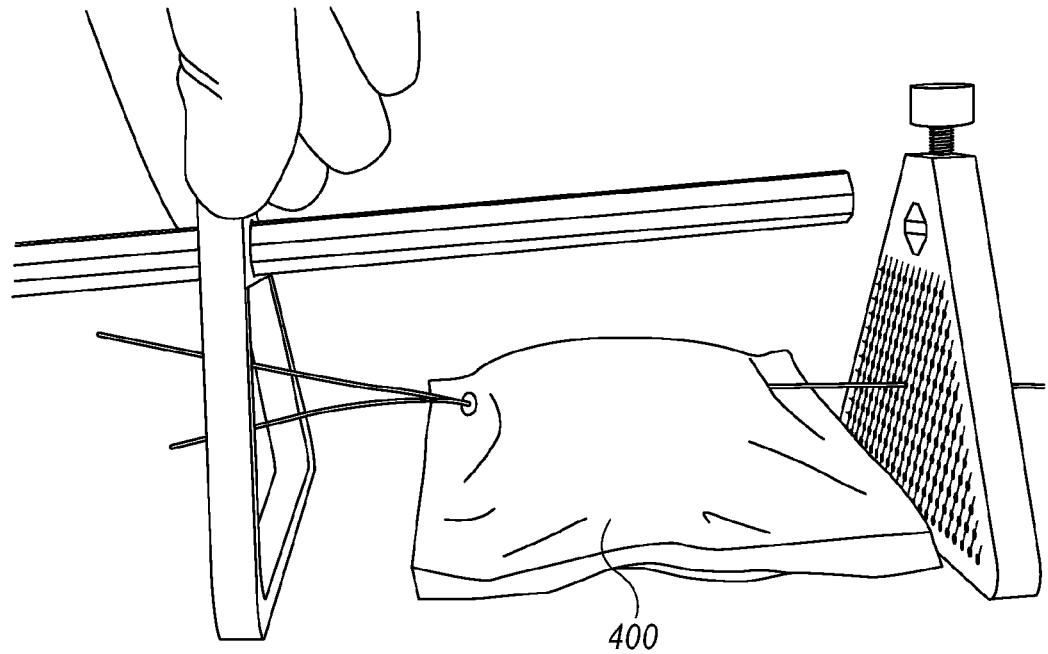

The method begins with grasping (302) the body organ between insertion grid plate 22 and frame plate 26, with leading grid plate 24 being placed behind frame plate 26, as shown in FIG. 5A. A plurality of applicators 410 which carry radiotherapy seeds mounted on leading wires therein are inserted (304) into the organ, through apertures 329 of insertion grid plate 22. Optionally, distal ends of the inserted applicators are passed through designated (e.g., corresponding) apertures 34 of leading grid plate 24, for accurate positioning of the applicators 410. Once a sufficient number of applicators 410 were passed through the organ, the applicators stabilize the organ and leading grid plate 24 is removed (306), as shown in FIG. 5B. The sufficient number of applicators 410 is optionally at least three, at least four, at least six, at least 10, at least 20 or even at least 50. In some embodiments, leading grid plate 24 is removed (306) only after all required applicators 410 are passed through the organ. The removal of leading grid plate 24 allows direct access by a physician or other medical practitioner to the organ and distal ends of the wires carrying the seeds. Optionally, the medical practitioner then ejects distal ends of the leading wires from the applicators 410, and grasps the leading wire through the central hole 72, to adjust (308) the longitudinal positioning of the seeds in the organ and/or anchor (310) the seeds in the organ 400, for example by fitting buttons on to the leading wires, as shown in FIG. 5C. After the leading wires are properly anchored, template assembly 20 is removed (312), as shown in FIG. 5D.

The applicators 410 and/or the anchoring of the seeds may be, for example, as described in PCT publication WO 2019/171308, titled: "Radiotherapy Seeds and Applicators", the disclosure of which is incorporated herein by reference in its entirety. It is noted, however, that any other suitable applicators and/or methods of implanting the seeds may be used with the radiotherapy template assembly 20, and the present invention is not limited to any specific acts performed using the increased accessibility provided by central hole 72.

Template assembly 20 may be used for treating of any organ which benefits from use of a template which holds the organ from two opposite sides, such as a breast, or limbs (e.g., arms, legs).

In the above description, the firm grasping of organ 400 is achieved by frame plate 26, which includes a closed frame defining a large central hole 72. In other embodiments, other elements are used to grasp the organ on the opposite side from insertion grid plate 22. For example, in some embodiments, frame plate 26 comprises an open frame, for example having a V-shape, an L-shape or a U-shape.

Figure 6:
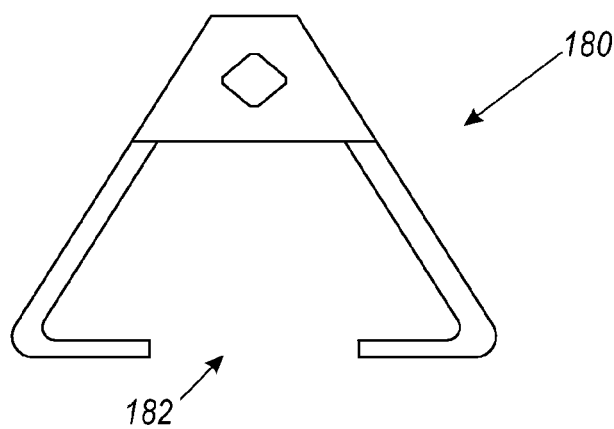
FIG. 6 is a schematic side view of an open-frame frame grid, in accordance with an embodiment of the invention.

FIG. 6 is a schematic side view of an open-frame frame grid 180, in accordance with an embodiment of the invention. Frame grid 180 has an opening 182, which allows for increased accessibility to the body organ. It is noted that opening 182 is not necessarily at the bottom of frame grid 180, as in some embodiments the opening 182 is at one side of the frame. Furthermore, in some embodiments, for example in a frame defining multiple medium size holes as shown in FIG. 3, the frame defines multiple openings.

While in the above description insertion grid plate 22, leading grid plate 24 and frame plate 26 are all mounted on the same bridge 28, in other embodiments only two of the plates are mounted on bridge 28, while a separate local element is used to attach leading grid plate 24 and frame plate 26. For example, frame plate 26 is optionally mounted on bridge 28, while leading grid plate 24 is connected to frame plate 26 by one or more separate local bridges. In another example embodiment, insertion grid plate 22 and leading grid plate 24 are mounted on bridge 28, and frame plate 26 is connected locally by one or more separate bridges to leading grid plate 24. In this embodiment, the leading grid plate 24 is not removed (306), as this may also remove frame plate 26, but rather leading grid plate 24 is merely retracted sufficiently relative to frame plate 26, so that the medical practitioner can conveniently access organ 400 through central hole 72 from above or below.

Figure 7:
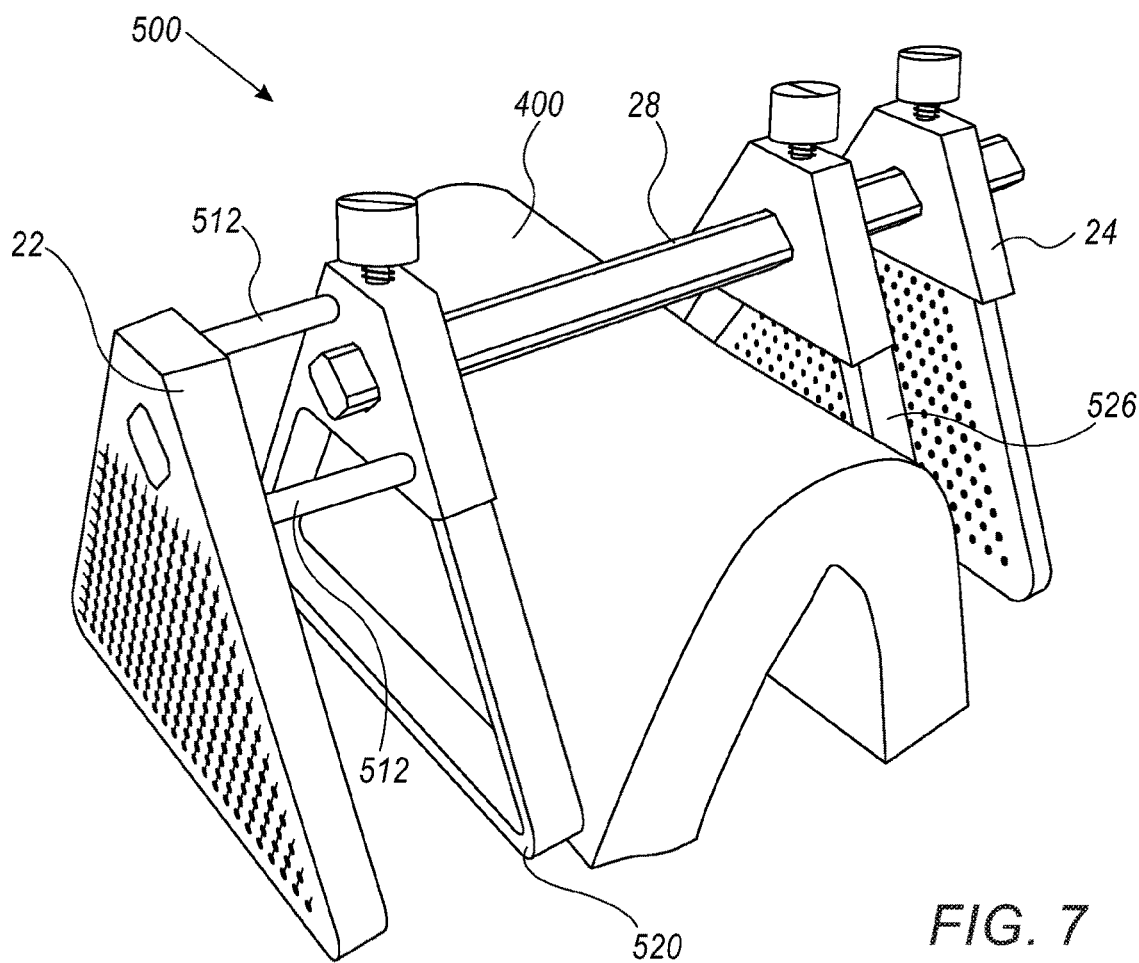
FIG. 7 is a schematic illustration of a radiotherapy template assembly, in accordance with another embodiment of the present invention.

FIG. 7 is a schematic illustration of a radiotherapy template assembly 500 with two frame plates 520 and 526, in accordance with an embodiment of the present invention. In the embodiment of FIG. 7, instead of only a single frame plate 26 (FIG. 1), assembly 500 includes two frame plates 520 and 526 for use on opposite sides of the organ 400. The organ 400 is sandwiched between the two frame plates 520 and 526, and the two frame plates 520 and 526 are located between the insertion grid plate 22 and the leading grid plate 24. A first frame plate 526 is located near leading grid plate 24 and a second frame plate 520 is located near insertion grid plate 22. Optionally, in accordance with this alternative, after removing leading grid plate 24 the seeds are anchored on the side from which the leading grid plate 24 was removed, through a central hole of the first frame plate 526. Then, the insertion grid plate 22 is removed and the seeds are anchored from the other side, through a central hole of the second frame plate 520. The order of removing the grid plates, may, however, be different.

In some embodiments, both frame plates 520 and 526 as well as both grid plates 22 and 24 are mounted on bridge 28. Alternatively, as shown in FIG. 7, grid plate 22 is connected to frame plate 520 by one or more, e.g., two, local bars 512.

Thus, grid plate 22 is removable without interaction with bridge 28. Further alternatively, grid plate 24 or both grid plates 22 and 24 are connected locally to their respective frame plate rather than through bridge 28.

While template assembly 20 is described as including two grid plates 22 and 24, this is not the case in all embodiments, as some embodiments include only a single grid plate, e.g., insertion grid plate 22.

Figure 8:
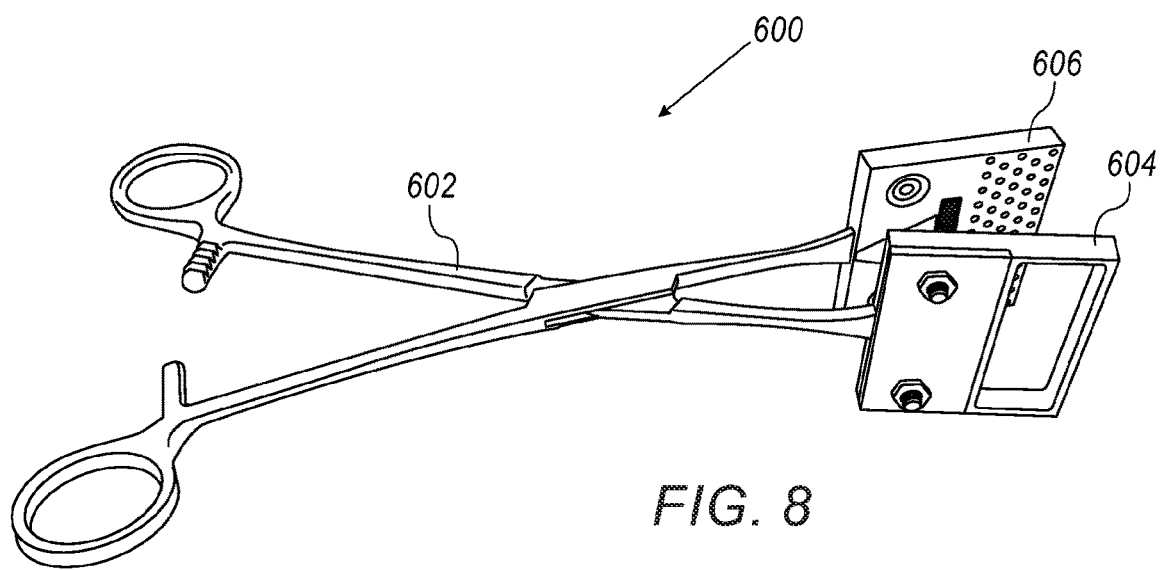
FIG. 8 is a schematic illustration of a radiotherapy template assembly, in accordance with still another embodiment of the present invention.

FIG. 8 is a schematic illustration of a radiotherapy template assembly 600 mounted on forceps 602, in accordance with an embodiment of the present invention. Template assembly 600 includes a grid plate 606 mounted on a distal end of a first arm of the forceps 602 and a frame plate 604 mounted on a distal end of a second arm of the forceps 602. By closing the forceps, the frame plate 604 and grid plate 606 are pressed against each other, and thus can firmly hold an organ located between them.

As shown, template assembly 600 includes only a single grid plate 606, which is used to direct the inserted applicators. While not using a second grid plate to receive the applicators inserted through grid plate 606 may reduce the accuracy of placement of the seeds, the advantage of the increased access provided by frame plate 604 was found by applicant to outweigh the reduced accuracy.

Alternatively, radiotherapy template assembly 600 includes an additional grid plate which is mounted on frame plate 604. After the applicators are inserted, the additional grid plate is removed to allow for anchoring the seeds. In other embodiments, two frame plates are used one on each arm of the forceps. A grid plate is mounted on one of the frame plates 604 or on both of the frame plates.

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. A template assembly, comprising:
a first grid for placement on a first side of a body organ, defining a first plurality of apertures adapted to receive elongate applicators;
a second grid for placement on a second side of the body organ, defining a second plurality of apertures, adapted to receive applicators passing through the first plurality of apertures of the first grid and the body organ; and
at least one closed frame defining an internal large hole, positioned between the first and second grids, such that applicators passing through the first plurality of apertures and the body organ also pass through the internal large hole, and wherein the at least one closed frame is configured to grasp the body organ.

2. The template assembly of claim 1, further comprising a bar on which the first grid, the second grid and the at least one closed frame are mounted.

3. The template assembly of claim 2, wherein the second grid is removably mounted on the bar.

4. The template assembly of claim 2, wherein the at least one closed frame is removably mounted on the bar.

5. The template assembly of claim 2, wherein the at least one frame is slidably mounted on the bar.

6. The template assembly of claim 1, wherein the large hole covers at least 25% of an area of the at least one closed frame.

7. The template assembly of claim 1, wherein the large hole covers at least 50% of an area of the at least one closed frame.

8. The template assembly of claim 1, wherein the at least one closed frame is coupled to the first grid through a first bridge and to the second grid through a second bridge, separate from the first bridge.

9. The template assembly of claim 1, wherein the at least one closed frame is configured to grasp the body organ, between the at least one closed frame and one of the first and second grids.

10. The template assembly of claim 1, wherein the at least one frame comprises a first frame and a second frame, each defining a large hole, wherein the first and second frames are positioned between the first and second grids, and wherein the body organ is grasped between the first frame and the second frame.

11. The template assembly of claim 1, wherein the applicators passing through the first plurality of apertures and received by the second plurality of apertures pass through the large hole.

12. A template assembly, comprising:
a first grid for placement on a first side of a body organ, defining a first plurality of apertures adapted to receive elongate applicators;
a second grid for placement on a second side of the body organ, defining a second plurality of apertures, adapted to receive applicators passing through the first plurality of apertures of the first grid and the body organ; and
at least one frame defining a large hole, positioned between the first and second grids and configured to grasp the body organ,
wherein the first and second grids and the at least one frame have a triangular shape.

13. A template assembly, comprising:
a first grid for placement on a first side of a body organ, defining a first plurality of apertures adapted to receive elongate applicators;
a second grid for placement on a second side of the body organ, defining a second plurality of apertures, adapted to receive applicators passing through the first plurality of apertures of the first grid and the body organ; and
a frame defining a large hole, positioned between the first and second grids and configured to grasp the body organ, between the frame and one of the first and second grids.

14. The template assembly of claim 13, wherein the at least one frame comprises an open frame.

15. The template assembly of claim 13, further comprising a bar on which the first grid, the second grid and the frame are mounted.

16. The template assembly of claim 15, wherein the at least one frame is slidably mounted on the bar.

17. The template assembly of claim 13, wherein the frame and the one of the first and second grids, grasp the organ from opposite sides of the body organ.

18. The template assembly of claim 13, wherein the large hole defined by the frame allows a physician access to the body organ.

\* \* \* \* \*